United States Patent [19]

Coupland et al.

[11] 4,248,720

[45] Feb. 3, 1981

[54] ORGANO MOLYBDENUM FRICTION-REDUCING ANTIWEAR ADDITIVES

[75] Inventors: Keith Coupland, Sarnia; Clinton R. Smith, Camlachie; Juan M. Salva, Sarnia, all of Canada

[73] Assignee: Exxon Research & Engineering Co., Florham Park, N.J.

[21] Appl. No.: 35,724

[22] Filed: May 3, 1979

Related U.S. Application Data

[63] Continuation-in-part of Ser. No. 843,964, Oct. 20, 1977, abandoned.

[51] Int. Cl.$^3$ .................. C10M 1/54; C10M 3/48; C01L 1/14; C07F 15/04
[52] U.S. Cl. .................. 252/42.7; 44/68; 252/32.7 E; 252/46.6; 260/429 D
[58] Field of Search ............... 252/32.7 E, 42.7, 46.6; 260/249 D; 44/68

[56] References Cited

U.S. PATENT DOCUMENTS

| | | | |
|---|---|---|---|
| 2,362,293 | 11/1944 | McNab et al. | 252/42.7 |
| 2,374,559 | 4/1945 | Morris et al. | 252/42.7 |
| 2,406,564 | 8/1946 | Rogers et al. | 252/42.7 |
| 2,804,431 | 8/1957 | Wythe | 252/46.6 |
| 3,223,625 | 12/1965 | Cyphers et al. | 252/18 |
| 3,541,014 | 11/1970 | LeSuer | 252/49.7 |

*Primary Examiner*—Curtis R. Davis
*Attorney, Agent, or Firm*—R. A. Dexter; J. J. Mahon

[57] ABSTRACT

A hydrocarbon-soluble molybdenum complex of a hydrocarbon substituted thio-bis-phenol, e.g. the reaction product of 1–2 moles of nonyl phenol sulfides and one mole of molybdenum oxide (reacted if desired in the presence of an amine promoter), in combination with a sulfur donor provides lubricity activity to lubricating oils and other hydrocarbons including fuels.

15 Claims, No Drawings

ORGANO MOLYBDENUM FRICTION-REDUCING ANTIWEAR ADDITIVES

CROSS-REFERENCE TO RELATED APPLICATION

This application is a continuation-in-part of Ser. No. 843,964 filed Oct. 20, 1977 now abandoned.

BACKGROUND OF THE INVENTION

The present invention relates to hydrocarbon soluble molybdenum complexes of thio-bis-phenols, their method of preparation and their utility as an additive for hydrocarbon compositions such as gasoline, fuel oil and lubricating oils including greases, industrial oils, gear oils and lubricants for engines and other equipment having moving parts operating under boundary lubricating conditions.

There are many instances, as is well known, particularly under "Boundary Lubrication" conditions where two rubbing surfaces must be lubricated, or otherwise protected, so as to prevent wear and to insure continued movement. Moreover, where, as in most cases, friction between the two surfaces will increase the power required to effect movement and where the movement is an integral part of an energy conversion system, it is most desirable to effect the lubrication in a manner which will minimize this friction. As is also well known, both wear and friction can be reduced, with various degrees of success, through the addition of a suitable additive or combination thereof, to a natural or synthetic lubricant. Similarly, continued movement can be insured, again with varying degrees of success, through the addition of one or more appropriate additives.

While there are many known additives which may be classified as antiwear, antifriction and extreme pressure agents and some may in fact satisfy more than one of these functions as well as provide other useful functions, it is also known that many of these additives act in a different physical or chemical manner and often compete with one another, e.g. they may compete for the surface of the moving metal parts which are subjected to lubrication. Accordingly, extreme care must be exercised in the selection of these additives to insure compatibility and effectiveness.

The metal dihydrocarbyl dithiophosphates are one of the additives which are known to exhibit antioxidant and antiwear properties. The most commonly used additives of this class are the zinc dialkyl dithiophosphates which are conventionally used in lubricant compositions. While such zinc compounds afford excellent oxidation resistances and exhibit superior antiwear properties, it has heretofore been believed that the same increases or significantly limits the ability to decrease friction between moving surfaces. As a result, compositions containing zinc dialkyl dithiophosphates were not believed to provide the most desirable lubricity and, in turn, it was believed that use of compositions containing the same would lead to significant energy losses in overcoming friction even when antifriction agents are included in the composition.

Known ways to solve the problem of energy losses due to high friction, e.g. in crankcase motor oils include the use of synthetic ester base oils which are expensive and the use of insoluble molybdenum sulfides which have the disadvantage of giving the oil composition a black or hazy appearance.

U.S. Pat. No. 3,047,500 is concerned with oil-soluble extreme pressure agents which are prepared from molybdenum pentachloride and an oil-soluble alkyl phenol, for instance a polyalkyl or dialkyl phenol containing a total of at least 6 carbon atoms in the side chain (col. 2, lines 15-20). Although the specification does not disclose or mention thio-bisphenols, it does teach that the molybdenum phenolate can be used in combination with an oil-soluble organic sulfur compound in the lubricating oil such as sulfurized sperm oil (see col. 3, lines 10-54 and Table I of col. 4).

U.S. Pat. No. 3,541,014 is concerned with oil-soluble molybdenum complexes prepared from molybdenum-containing anions and assorted overbased materials. The promoters for the preparation of these molybdenum complexes include mono- and dialkylated phenols which appear to be retained in the overbased mixture (see col. 5, lines 58-67).

Other types of molybdenum compounds taught to be useful in lubricating oils include the alkyl esters of molybdic acid as corrosion inhibitors (see U.S. Pat. No. 2,805,997) which appear to be hydrolytically unstable and nitrogenous thiomolybdates as metal antiwear additives which are said to function by providing a coating of reduced coefficient of friction (see U.S. Pat. No. 2,938,869). Chloromolybdenum esters of phenols are taught to be useful as extreme pressure additives for lubricants (U.S. Pat. No. 3,047,506) although the presence of chlorine can be a cause of corrosion in crankcase lubricants. Another extreme pressure additive is taught in the form of an oil-soluble molybdenum complex produced by the displacement of carbonate from an overbased metal detergent with a molybdenum-containing anion (U.S. Pat. No. 3,541,014).

Similarly, antifriction agents or oiliness or lubricity agents as the same are often referred to in the prior art, function by forming a coating on the surface of the moving metal parts. As in the case of antiwear agents, however, the coating bonds are, generally, effected physically, rather than chemically, and, indeed, the bonding between an antifriction agent and the surface is, generally, weaker than the bond formed between an antiwear agent and the metal surface.

In light of the foregoing, the need for improved lubricating compositions that will permit operation of moving parts under boundary conditions with reduced friction is believed to be readily apparent. Similarly, the need for such a composition that can include conventional base oils and other conventional additives and can be used without the loss of other desirable lubricant properties, particularly those provided by zinc dialkyl dithiophosphates, is also readily apparent.

SUMMARY OF THE INVENTION

It has now surprisingly been discovered that the foregoing and other disadvantages of the prior art lubricating additives and lubricating compositions formulated therewith can be overcome with a novel class of organo molybdenum complexes believed to be represented by the following formula I:

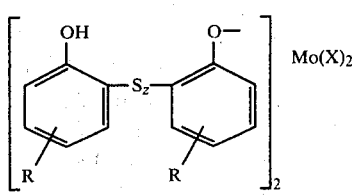

where z is 1–3, X is selected from sulfur or oxygen and R is a substantially hydrocarbyl group containing from 1 to 50, preferably 7 to 28, optimally 8 to 12 carbon atoms. These complexes are particularly useful when used in combination with a sulfur donor, e.g. zinc dialkyl dithiophosphate. It is understood that the R substituent can contain substituted pendant hetero groups provided they do not detrimentally alter the hydrocarbon solubility of the molybdenum complex.

In accordance with the present invention, the foregoing and other objects and advantages are accomplished with a hydrocarbon composition comprising a major portion of a hydrocarbon, e.g. a lubricating oil and at least a friction reducing amount of said hydrocarbon soluble molybdenum complex and preferably a lubricity enhancing combination of: (a) said hydrocarbon soluble molybdenum complex; and (b) an oil-soluble sulfur donor, preferably zinc dialkyl dithiophosphate, and, if desired, at least a sludge-dispersing amount of an oil-soluble dispersant, e.g. an ashless dispersant and at least a rust-inhibiting amount of a rust inhibitor. In practice, the lubricity enhancing combination is present in an amount sufficient to provide from about 0.005 to 0.2, preferably 0.03 to 0.15, optimally about 0.1, wt.% molybdenum and at least about 0.25, e.g. 0.25 to 1, wt.% sulfur donor, all weight percent being based on the total weight of the oil composition.

DETAILED DESCRIPTION OF THE INVENTION OIL-SOLUBLE ORGANO MOLYBDENUM COMPOUND

As earlier described, the hydrocarbon-soluble molybdenum complexes of the invention are believed to conform to said Formula I. The R group of said Formula I as defined is substantially hydrocarbyl and thus is alkyl, aryl, aralkyl, cycloalkyl, or alkaryl; however, the hydrocarbyl group may contain polar substituents such as amino, aminoalkyl, hydroxy, hydroxyalkyl, halo, mercapto, keto, phosphinyl, phosphoryl, thiophosphoryl and dithiophosphoryl radicals.

Specific examples of the R group includes methyl, ethyl, propyl, isopropyl, isobutyl, n-butyl, sec-butyl, tert-butyl, n-hexyl, heptyl, octyl, nonyl-decyl, dodecyl, tridecyl, heptadecyl, octadecyl, polyisobutenyl, polypropylene.

The organic molybdenum complexes are the reaction product of a hydrocarbon substituted thio-bis-phenol and a source of molybdenum. The aforesaid thio-bis-phenols can be characterized by Formula II:

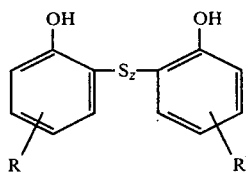

wherein R and z are each the same as previously described. These thio-bis-phenols are readily produced from the reaction of alkyl phenols and a source of sulfur, e.g. chemical sulfur or sulfur halides.

A particularly useful reactant for the preparation of the molybdenum complex can be characterized by Formula III.

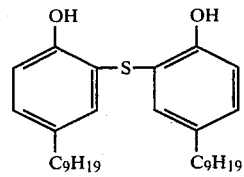

from which the structure of the preferred complex is obtained and believed to be the structure of Formula IV:

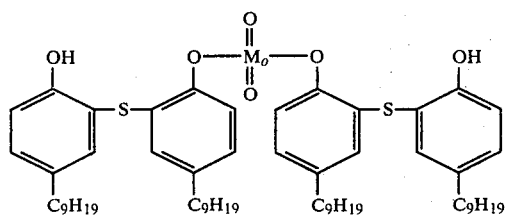

The source of molybdenum is a molybdenum oxygen or sulfur-containing compound capable of reacting with the thio-bis-phenol to provide a molybdenum complex containing from about 0.5 to 20, preferably 2 to 10, optimally about 5 wt.% molybdenum based on the total weight of said complex. The sources of molybdenum include molybdic trioxide (also known as molybdic anhydride) ammonium thiomolybdate, ammonium bismolybdate, molybdenum halides, and ammonium heptamolybdate tetrahydrate.

The organomolybdenum complex is substantially the product of reaction between 1–2 moles substituted thio-bis-phenol and 1 mole of molybdenum metal derived from the molybdenum source. The reaction is readily carried out by reaction at elevated temperature to accelerate said reaction and remove the water of reaction. The reaction is carried out in an inert solvent such as a light aromatic solvent, e.g. toluene or light hydrocarbon oil or without solvent. The reaction can, therefore, be conducted at from about 80° C. to 250° C. for a period of from about 0.5 to 40 hours and/or at least until the required amount of water of reaction is removed, as by nitrogen sparging or distillation at atmospheric or reduced pressure. The reaction may be catalyzed by the inclusion in the said reaction mixture of a suitable promoter. Examples of suitable promoters or catalysts are drawn from alcohols and amines. Particularly suitable are glycols, diamines or alkanolamines. Illustrative of such promoters are: glycols, e.g. ethylene glycol, propylene glycol, butylene glycol, hexylene glycol, catechols and alkylated catechols, polyamines, e.g. ethylene diamine, diethylene triamine, triethylene tetramine, tetraethylene pentramine, pentaethylene hexamine and mixtures of such polyamines formed from the reaction of ethylene dichloride and ammonia or ethylene imine and ammonia, alkanolamines, e.g. ethanolamine diethanolamine, triethanolamine, hydroxyethyl ethylene diamine and the reaction product of alkylene oxides such as ethylene oxide or propylene oxide with polyamines.

SULFUR DONORS

It has been discovered that the novel class of hydrocarbon-soluble organo molybdenum complexes provide suitable lubricity improvement in lubricating oils when used in combination with an active sulfur donor which can be defined as a compound which when used in admixture with said molybdenum complex reduces the coefficient of friction at least about 10%. The active sulfur donor is present in an amount of from about 0.1 to 10, preferably 0.2 to 2, parts by weight per part by weight of molybdenum complex.

Illustrative of active sulfur donors are metal dihydrocarbyl dithiophosphates and the corresponding precursor esters, phosphosulfurized pinenes, sulfurized olefins and hydrocarbons, sulfurized fatty esters and sulfurized alkyl phenols.

Preferred are the zinc dihydrocarbyl dithiophosphates which are salts of dihydrocarbyl esters of dithiophosphoric acids and may be represented by the following Formula V:

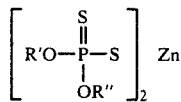

wherein R' and R" may be the same or different hydrocarbyl radicals containing from 1 to 18 and preferably 2 to 12 carbon atoms and including radicals such as alkyl, alkenyl, aryl, aralkyl, alkaryl and cycloaliphatic radicals. Particularly preferred as R and R' groups are alkyl groups of 2 to 8 carbon atoms. Thus, the radicals may, for example, be ethyl, n-propyl, i-propyl, n-butyl, i-butyl, sec-butyl, tert-butyl, amyl, n-hexyl, i-hexyl, n-heptyl, n-octyl, decyl, dodecyl, octadecyl, 2-ethylhexyl, phenyl, butylphenyl, cyclohexyl, methylcyclopentyl, propenyl, butenyl, etc. In order to obtain oil solubility, the total number of carbon atoms in the dithiophosphoric acid will average about 5 or greater.

The zinc dihydrocarbyl dithiophosphates which are useful as the coadditive, i.e. sulfur donor of the present invention may be prepared in accordance with known techniques by first esterifying a dithiophosphoric acid usually by reaction of an alcohol or phenol with $P_2S_5$ and then neutralizing the dithiophosphoric acid ester with a suitable zinc compound such as zinc oxide.

In general, the zinc dihydrocarbyl dithiophosphate will be used in the lubricating composition at a concentration within the range of about 0.01 to about 5 parts by weight per 100 parts of lubricating oil and preferably from about 0.5 to about 1.5. This is adequate for sulfur donation whereby the lubricity enhancement of the lubricating oil composition by the coadditive combination is realized.

As noted earlier, an equally suitable active sulfur donor is the dihydrocarbyl esters of dithiophosphoric acid which may be represented by the Formula VI:

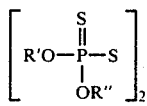
VI where R' and R" as previously defined. Particularly useful is the dibutylphenyl dithiophosphate.

The phosphorosulfurized terpenes as represented by pinene, dipenene, allo-ocimene, etc., are another group of dithiophosphate diesters which are active sulfur donors. Of the terpenes, the bicyclic pinene is preferred. The phosphosulfurized terpene is readily obtained by reaction of about one mole of diester of thiophosphoric acid and one mole of pinene at a temperature of at least 100° C., e.g. 100° C. to 200° C. The preferred active sulfur donor can be characterized as the bornyl ester of dihydrocarbyl ($C_2$–$C_{20}$) dithiophosphoric acids (as shown in U.S. Pat. No. 2,689,258).

The sulfurized olefins and hydrocarbons are further esters of thiophosphoric acids which are useful sulfur donors. These esters are achieved by reaction with olefins such as ethylene, propylene, isobutylene, decene, dodecene, octadecene, etc., olefin polymers of molecular weight ranging from 100 to 50,000 such as ethylene, propylene, isobutylene, etc., aromatics such as benzene, naphthylene, toluene, xylene, etc., petroleum fractions and condensation products of halogenated aliphatic hydrocarbons with aromatic compounds, e.g. wax naphthalene (see U.S. Pat. No. 2,804,431).

The sulfurized fatty esters are another subclass of esters which are active sulfur donors. These products are readily obtained from the reaction of $P_2S_5$ and aliphatic alcohols usefully having from about 8 to 22 carbons obtained from natural sources including linoleic, palmolitic, behenic, stearic, palmitic, lauric, capric, etc., as well as mixtures obtained from vegetable and animal oils such as tall oil.

The sulfurized alkyl phenols are generally $C_4$ to $C_{20}$ alkyl phenol sulfides. These sulfurized alkyl phenols are readily produced by sulfurizing an alkyl phenol with a sulfur halide or elemental sulfur.

Other Additives For Lubricating Compositions

In addition to the organo molybdenum complex and active sulfur donor, the lubricating oil composition may contain other well known lubricating oil additives to provide trouble-free operation of the lubricated equipment, such as ashless dispersants, metallic detergents, supplemental oxidation and corrosion inhibitors, extreme pressure agents, rust inhibitors, pour point depressants, viscosity index improvers, etc.

1. Ashless Dispersants

As used herein, the terminology "ashless dispersant" is intended to describe the now well-known class of non-metal-containing oil-soluble polymeric additives or the acyl derivatives of relatively high molecular weight carboxylic acids which are capable of dispersing contaminants and the like in hydrocarbons such as lubricating oils. The carboxylic acids may be mono- or polycarboxylic acids and they are generally characterized by substantially hydrocarbon constituents containing an average of 50 to 250 aliphatic carbon atoms.

A preferred class of ashless dispersants are the nitrogen-containing dispersant additives which are generally known in the art as sludge dispersants for crankcase motor oils. These dispersants include mineral oil-soluble salts, amides, imides and esters made from high molecular weight mono- and dicarboxylic acids (and where they exist the corresponding acid anhydrides) and various amines of nitrogen-containing materials having amino nitrogen or heterocyclic nitrogen and at least one amido or hydroxy group capable of salt, amide, imide or ester formation. Usually, these dispersants are made by condensing a monocarboxylic acid or a dicarboxylic acid or anhydride, preferably a succinic acid producing material such as alkenyl succinic anhydride, with an amine or alkylene polyamine. Usually, the molar ratio of acid or anhydride to amine is between 1:1 to 5:1.

Primarily because of its ready availability and low cost, the hydrocarbon portion of the mono-, or dicarboxylic acid or anhydride is preferably derived from a polymer of a $C_2$ to $C_5$ monoolefin, said polymer generally having between 50 and 250 carbon atoms. A particularly preferred polymer is polyisobutylene.

Polyalkyleneamines are usually used to make the non-metal-containing dispersant. These polyalkyleneamines include those represented by the general formula:

$$NH_2(CH_2)_n\text{—}[NH(CH_2)_n]_m\text{—}NH$$

wherein n is 2 to 3 and m is a number from 0 to 10. Specific compounds coming within the formula include diethylenetriamine, tetraethylenepentamine, dipropylenetriamine, octaethylenenonamine, and tetrapropylenepentamine; N,N-di(2-aminoethyl) ethylenediamine may also be used. Other aliphatic polyamino compounds that may be used are N-amino-alkylpiperazines, e.g. N-(2-aminoethyl) piperazine. Mixtures of alkylene polyamines approximating tetraethylenepentamine are commercially available, e.g. Dow E-100 sold by Dow Chemical Company of Midland, Michigan.

Representative dispersants are formed by reacting about one molar amount of polyisobutenyl succinic anhydride with from about one to about two molar amounts of tetraethylenepentamine or with from about 0.5 to 1 moles of a polyol, e.g. pentaerythritol.

It is possible to modify the ashless dispersants generally by the addition of metals such as boron in order to enhance the dispersancy of the additive. This is readily accomplished by adding boric acid to the reaction mixture after the imidation or esterification is substantially complete and heating the mixture at temperatures of 100° to 150° C. for a few hours.

2. Other Additives

Detergents useful in conjunction with dispersants, preferably the ashless type, include normal, basic or overbased metal, e.g. calcium, magnesium, etc., salts of petroleum naphthenic acids, petroleum sulfonic acids, alkyl benzene sulfonic acids, oil-soluble fatty acids, alkyl salicyclic acids, alkyl phenols, alkylene-bisphenols, and hydrolyzed phosphorosulfurized polyolefins.

Oxidation inhibitors include phenols, amines, sulfurized phenols and alkyl phenothiazines.

Pour point depressants include wax alkylated aromatic hydrocarbons, olefin polymers and copolymers, acrylate and methacrylate polymers and copolymers.

Viscosity Index Improvers include olefin polymers such as polybutene, ethylene-propylene copolymers, hydrogenated polymers and copolymers and terpolymers of styrene with isoprene and/or butadiene, polymers of alkyl acrylates or alkyl methacrylates, copolymers of alkyl methacrylates with N-vinyl pyrrolidone or dimethylaminoalkyl methacrylate, post-grafted polymers of ethylenepropylene with an active monomer such as maleic anhydride which may be further reacted with an alcohol or an alkylene polyamine, styrene/maleic anhydride polymers post-reacted with alcohols and amines, etc.

The hydrocarbons in which the additive combination of the invention is most effective are mineral oils having a viscosity as measured by ASTM D-445 of from about 2 to 40, preferably 5 to 20 centistokes at 99° C.

If the additive combination of oil-soluble organo molybdenum complex and active sulfur donor are used as an additive concentrate, the concentrate may consist essentially of from about 5 to 80% of the additive combination, the remainder being a satisfactory solvent such as kerosene, mineral oil, a naphtha and the like. The preferred concentrate contains about 10 to 60% of the additive combination in the solvent.

Whether the organo molybdenum complex is used alone or in combination with an active sulfur donor, its concentration may vary appreciably with the particular hydrocarbon. For example, when said molybdenum complex is used alone in a fuel such as gasoline, the concentration of the complex ranges from 10 to 1,000, preferably 20 to 50 weight parts per million based on the total weight of the fuel composition, whereas as a lubricant, it is used in combination with the active sulfur donor, which combination ranges from about 0.5 to 5, preferably 1 to 3 wt.% based on the total weight of the lubricating oil.

The invention will be further understood by reference to the following examples which illustrate a preferred form of the invention and compares the same with different, though similar compositions.

The following examples illustrate more clearly the compositions of the present invention. However, these illustrations are not to be interpreted as specific limitations on this invention.

EXAMPLE 1

Nonyl phenol sulfide (100 g), diluent oil (100 g) $C_{24}$-alkyl benzene sulfonic acid (10 g) were stirred together and heated to 100° C. Ammonium heptamolybdate tetrahydrate (37.5 g) was added and the temperature raised to 150° C. During this time, ethanolamine (10 g) was added. The temperature was raised to 175° C. for 4 hours. The volatile material was removed via a distillation head and the product isolated by filtration to yield a dark viscous product containing 3.1 wt.% Mo.

EXAMPLE 2

Nonyl phenol sulfide (100 g), diluent oil (100 g) were stirred and heated to 100° C. Ammonium heptamolybdate tetrahydrate (18.75 g) and three drops of a silicone defoamer were added. Ethanolamine (13 g) was added slowly while raising the temperature to 150° C. After heating at 175° C. for 4 hours, the product was isolated by filtration to yield a dark product containing 4.14 wt.% Mo. During the reaction, 3.5 cm³ of water was removed.

EXAMPLE 3

Nonyl phenol sulfide (100 g), diluent oil (100 g) were heated together at 100° C. Ammonium heptamolybdate tetrahydrate (18.75 g) and four drops of silicone antifoam were added while raising the temperature to 150° C. Ethylene diamine (12.8 g) was added dropwise and the temperature was maintained for 4 hours. During this period, 4.5 cm³ of water was removed. The product, a dark viscous material, was isolated by filtration; it contained 4.25 wt.% Mo.

EXAMPLE 4

Nonyl phenol sulfide (500 g) and diluent oil (500 g) were stirred together and heated to 100° C. Ammonium heptamolybdate tetrahydrate (187.5 g) and silicone defoamer (5 drops) were added and the temperature raised slowly with addition of ethanolamine. During this period (9 hours), water was removed by distillation. Reaction was completed by heating to 175° C. for 4 hours then the product was isolated by filtration. The product (950 g) was a black viscous liquid containing 3.2 wt.% Mo.

EXAMPLE 5

Nonyl phenol sulfide (100 g) diluent oil (100 g) and molybdic trioxide (15.1 g) were stirred together and heated to 100° C. Ethylene diamine (12.8 g) was added dropwise and the temperature raised to 175° C. for 4 hours. Water (2.8 cm$^3$) was removed by distillation and the product isolated by filtration to yield a product (162.8 g) containing 4.29 wt. % Mo.

EXAMPLE 6

Nonyl phenol sulfide (100 g), diluent oil (100 g) and molybdic trioxide (15.1 g) were stirred together and heated to 100° C. Diethylene triamine (21.9 g) was added slowly and the temperatures raised to 175° C. for 4 hours. The product was isolated by filtration to yield a viscous black oil containing 3.85 wt. % Mo.

EXAMPLE 7

Nonyl phenol sulfide (100 g), diluent oil (100 g) and molybdic trioxide (15.1 g) were heated together, with stirring, at 100° C. Diethylene triamine (14.6 g) was run in and the temperature raised to 175° C. for 4 hours. During this time, water (1.6 cm$^3$) was distilled out. The product (178 g) was isolated by filtration. It was a dark viscous oil containing 3.85 wt. % Mo.

EXAMPLE 8

The procedure of Example 7 was followed except that only 7.3 g diethylene triamine was used as catalyst. The product contained 3.06 wt. % Mo.

EXAMPLE 9

The procedure of Example 7 was followed except no catalyst was added. The product did not contain molybdenum.

EXAMPLE 10

Nonyl phenol sulfide (550 g), diluent oil (550 g) and molybdic trioxide (84.2 g) were heated together with stirring at 100° C. Ethanolamine (72.5 g, 95% pure) was added dropwise and the temperature raised to 175° C. for 4 hours. During the reaction, 22 cm$^3$ of volatiles were removed by distillation. The product (1111 g) was isolated by filtration to yield a dark viscous oil containing 4.16 wt. % Mo (representing a conversion of Mo of 93%).

EXAMPLE 11

Nonyl phenol sulfide (550 g), diluent oil and molybdic trioxide (84.2 g) were heated together with stirring at 100° C. Ethylene diamine (70.3 g) was added to the mixture maintaining the temperature between 120°-130° C. The temperature was raised to 175° C. for 4 hours. During the reaction, volatile material was distilled from the reaction mixture. The product contained, after filtration, 4.4 wt. % Mo (100% conversion).

EXAMPLE 12

The procedure of Example 11 was followed substituting ammonium heptamolybdate tetrahydrate (103.2 g) as the source of molybdenum. The product contained 4.33 wt. % Mo (96.8% conversion).

EXAMPLE 13

The procedure of Example 10 was followed substituting ammonium heptamolybdate tetrahydrate (103.2 g) as the source of molybdenum. The product contained 4.36 wt. % Mo (97.9% conversion).

EXAMPLE 14

A lubricating oil composition was prepared by blending together the individual components, noted below, usually at a slightly elevated temperature, i.e. from about 45° C. to above 65° C. to insure complex mixing. The final composition of Example 14 formulated into 10W/30 SE quality automotive engine oils was as follows:

| Blend 14 | |
|---|---|
| Wt. % Active Ingredient | |
| Mineral Oil | 94.9 |
| Ashless Dispersant | 2.9 |
| Magnesium Sulfonate | 0.2 |
| ZDDP[1] | 0.9 |
| Rust-Inhibitor | 0.1 |
| Viscosity Index Improvers | 1.0 |
| Silicone Defoamer | 0.01 |
| Ashless Antioxidant | — |
| Metal Detergent-Inhibitor | — |

[1]Zinc dihydrocarbyl dithiophosphate such as zinc dinonyl phenol dithiophosphate This formulated blend was itself and in modified form according to the teachings of this invention subjected to testing as hereinafter set forth:

1. Testing Procedure A

The Roxana Four-ball wear tester with the Brown/GE modification from Roxana Machine Works, St. Louis. MO. was used to measure friction properties by the following procedure. The tester was assembled in the normal wear procedure as described in ASTM D2266-67 using four ½" bearing steel balls. The tester was brought to 110° C. and run at 1200 rpm and 15 kg for a minimum of 45 minutes. If the frictional force as seen on the strip chart recorder is constant for the last 10 minutes, the speed is reduced to 25 rpm. Otherwise, the test is carried on until frictional force has stabilized. The test at 25 rpm is carried out at 110° C. and 15 kg for 15 minutes or until frictional force has stabilized.

The compounds of the invention were then evaluated by subjecting the products to a study of their utility as a lubricity enhancing and/or antiwear additive for lubricating oils by using the Testing Procedure A. The weight percentage of amounts of molybdenum complex added is given in amount of complex added.

The results of tests under Procedure A are set forth in Table I.

From the foregoing, it is shown that the additives of the invention provide lubricity enhancement to lubricating oils when an active sulfur donor is present and that they have utility as additives for lubricating oils.

It is to be understood that the examples present in the foregoing specification are merely illustrative of this invention and are not intended to limit it in any manner; nor is the invention to be limited by any theory regarding its operability. The scope of the invention is to be determined by the appended claims.

TABLE I

| Test | Lubricant | Added Mo Complex Example # | Wt (%) | Coefficient of Friction 46 cm/sec | 1 cm/sec | Friction Reduction (%) 46 cm/sec | 1 cm/sec |
| --- | --- | --- | --- | --- | --- | --- | --- |
| 1 | 14 | — | — | 0.084 | 0.115 | — | — |
| 2 | 14 | 10 | 1.1 | 0.046 | 0.077 | 45.6 | 33.5 |
| 3 | 14 | 10 | 1.7 | 0.043 | 0.073 | 49.4 | 36.7 |
| 4 | 14 | 11 | 1.1 | 0.050 | 0.060 | 40.5 | 48.3 |
| 5 | 14 | 11 | 1.7 | 0.044 | 0.062 | 48.1 | 46.4 |
| 6 | 14 | 12 | 1.1 | 0.045 | 0.061 | 46.2 | 47.3 |
| 7 | 14 | 12 | 1.7 | 0.041 | 0.061 | 50.7 | 47.3 |
| 8 | 14 | 13 | 1.1 | 0.061 | 0.085 | 27.9 | 26.4 |
| 9 | 14 | 13 | 1.7 | 0.050 | 0.077 | 40.5 | 33.4 |

What is claimed is:

1. An organo molybdenum complex represented by the formula

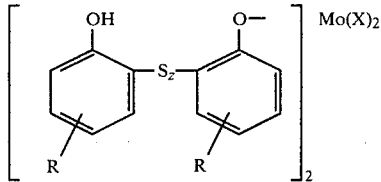

wherein R is a substantially hydrocarbyl group containing from 1 to 50 carbon atoms, z is 1–3 and X is selected from sulfur or oxygen.

2. An organo molybdenum complex according to claim 1 wherein R is an alkyl group containing from about 7 to 28 carbon atoms and X is oxygen.

3. A hydrocarbon-soluble organo molybdenum complex obtained as the reaction product of a $C_1$ to $C_{50}$ hydrocarbyl substituted thio-bis-phenol with about 0.5 molar equivalent of a molybdenum source of the class consisting of molybdic trioxide, ammonium thiomolybdate, ammonium bismolybdate, molybdenum halides and ammonium heptamolybdate tetrahydrate while in the presence of a promoting agent the promoting agent being a glycol, a polyamine, an alkanolamine or a phenol.

4. A complex according to claim 3 wherein said thio-bis-phenol is nonyl phenol sulfide, the said molybdenum source is molybdic trioxide and the promoter is ethylenediamine.

5. A complex according to claim 3 wherein said thio-bis-phenol is nonyl phenol sulfide, the said molybdenum source is ammonium heptamolybdate tetrahydrate and the promoter is ethylenediamine.

6. A complex according to claim 3 wherein said thio-bis-phenol is nonyl phenol sulfide, the said molybdenum source is molybdic trioxide and the promoter is ethanolamine.

7. A complex according to claim 3 wherein said thio-bis-phenol is nonyl phenol sulfide, the said molybdenum source is ammonium heptamolybdate tetrahydrate and the promoter is ethanolamine.

8. A hydrocarbon composition comprising a major portion of a hydrocarbon and at least a friction-reducing amount of the combination of: (a) an organo molybdenum complex represented by the formula:

$$\left[ \begin{array}{c} \text{OH} \quad \text{O} \\ \bigcirc\!\!-\!\!S_z\!\!-\!\!\bigcirc \\ R \quad R \end{array} \right]_2 Mo(X)_2$$

where z is 1–3 and X is selected from oxygen or sulfur and R is a substantially hydrocarbyl group containing from 1 to 50 carbon atoms; and (b) an oil-soluble active sulfur donor being a metal dihydrocarbyl dithiophosphate or dithiophosphoric ester, a phosphosulfurized pinene, a sulfurized olefin or hydrocarbon, a sulfurized fatty ester or a sulfurized alkyl phenol, said combination providing from about 0.005 to 0.2 weight percent molybdenum and said sulfur donor being present in at least 0.25 weight percent, all of said weight percents being based on the total weight of said composition.

9. A hydrocarbon composition according to claim 8 wherein said hydrocarbon is mineral oil, said organo complex is an oil-soluble reaction product of a $C_7$–$C_{28}$ hydrocarbyl substituted thio-bis-phenol with about 0.5 molar equivalent of a molybdenum source of the class consisting of molybdic trioxide, ammonium thiomolybdate, ammonium bismolybdate, molybdenum halides, and ammonium hertamolybdate tetrahydrate prepared in the presence of a promoting agent, the promoting agent being an amine, an alcohol, a phenol, a diamine, a glycol, or an alkanolamine, and said sulfur donor is an oil-soluble dihydrocarbyl ester of dithiophosphoric acid or metal dihydrocarbyl dithiophosphate.

10. A hydrocarbon composition according to claim 9 wherein said mineral oil has a viscosity as measured by ASTM D-445 of from about 2 to 40 centistokes at 99° C., said thio-bis-phenol is nonyl phenol sulfide, said molybdenum compound is ammonium heptamolybdate tetrahydrate, said promoting agent is ethanolamine, and said active sulfur donor is zinc dihydrocarbyl dithiophosphate present in an amount of from 0.2 to 2 parts by weight per part by weight of said molybdenum complex.

11. A hydrocarbon composition according to claim 9 wherein said mineral oil has a viscosity as measured by ASTM D-445 of about from 2–40 centistokes at 99° C., said thio-bis-phenol is nonyl phenol sulfide, said molybdenum source is ammonium heptamolybdate tetrahydrate, said promoting agent is ethylene diamine, and said active sulfur donor is zinc dihydrocarbyl dithiophosphate present in an amount of 0.2–2.0 parts by weight of said molybdenum complex.

12. A hydrocarbon composition according to claim 9 wherein said mineral oil has a viscosity as measured by ASTM D-445 of about from 2–40 centistokes at 99° C., said thio-bis-phenol is nonyl phenol sulfide, said molybdenum source is molybdic trioxide, said promoting agent is ethanolamine, and said sulfur donor is zinc dihydrocarbyl dithiophosphate present in an amount of from 0.2–2 parts by weight per part by weight of molybdenum complex.

13. A hydrocarbon composition according to claim 9 wherein said mineral oil has a viscosity as measured by ASTM D-445 of about from 2–40 centistokes at 99° C., said thio-bis-phenol is nonyl phenol sulfide, said molybdenum source is molybdic trioxide, said promoting agent is ethylene diamine and said active sulfur donor is zinc dihydrocarbyl dithiophosphate present in an amount of from 0.2–2 parts by weight per part by weight of molybdenum complex.

14. A concentrate consisting essentially of from 5 to 80 weight percent of the combination of a hydrocarbon soluble organo molybdenum complex obtained as the reaction product of a $C_7$–$C_{28}$ hydrocarbyl substituted thio-bis-phenol with about 0.5 molar equivalent of a molybdenum source of the class consisting of molybdic trioxide, ammonium thiomolybdate, ammonium bismolybdate, molybdenum halides, and ammonium heptamolybdate tetrahydrate and from about 0.1 to 10 parts by weight of active sulfur donor per part by weight of said complex and 20 to 95 weight percent of a solvent for said combination, said sulfur donor being a dihydrocarbyl dithiophosphate or dithiophosphoric ester, a phosphosulfurized pinene, a sulfurized olefin or hydrocarbon, a sulfurized fatty ester, or a sulfurized alkyl phenol.

15. A gasoline having improved antiwear properties containing from 10 to 1,000 parts per million of an organo molybdenum complex represented by the formula:

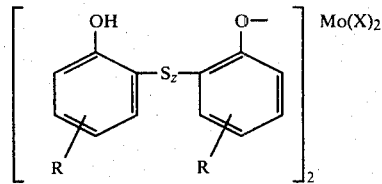

wherein R is a substantially hydrocarbyl group containing from 1 to 50 carbon atoms, z is 1–3 and X is selected from sulfur or oxygen.

* * * * *